United States Patent [19]
Bryars et al.

[11] Patent Number: 5,807,267
[45] Date of Patent: Sep. 15, 1998

[54] HEART PULSE MONITOR

[75] Inventors: John D. Bryars, Encinitas; David Cavanaugh, San Diego, both of Calif.

[73] Assignee: Advanced Body Metrics Corporation, Rancho Santa Fe, Calif.

[21] Appl. No.: 512,712

[22] Filed: Aug. 8, 1995

Related U.S. Application Data

[63] Continuation-in-part of Ser. No. 462,152, Jun. 5, 1995, which is a continuation of Ser. No. 252,605, Jun. 1, 1994, abandoned.

[51] Int. Cl.[6] ........................................... A61B 5/00
[52] U.S. Cl. ..................... 600/500; 600/477; 600/479; 600/503
[58] Field of Search .................... 128/672, 666, 128/687–690, 706, 707; 600/500–503; 5/476–475

[56] References Cited

U.S. PATENT DOCUMENTS

| | | | |
|---|---|---|---|
| 5,000,188 | 3/1991 | Kojima | 128/687 |
| 5,197,489 | 3/1993 | Conlan | 128/690 |
| 5,243,992 | 9/1993 | Eckerle et al. | 128/690 |
| 5,301,154 | 4/1994 | Suga | 128/690 |
| 5,431,170 | 7/1995 | Mathews | 128/666 |
| 5,539,706 | 7/1996 | Takenaka et al. | 128/690 |
| 5,558,096 | 9/1996 | Palatnik | 128/687 |

*Primary Examiner*—Robert L. Nasser
*Attorney, Agent, or Firm*—G. Donald Weber, Jr.

[57] ABSTRACT

The invention herein described is intended to provide the user with a reliable heart rate monitor that is a completely self contained unit and is capable of providing accurate readings while the wearer is moving about. The use of piezoelectric sensing elements eliminates the power drain caused by LEDs and similar devices. The sensing element mounting means disclosed herein is devised to greatly reduce the noise introduced into the pulse signal by body motion. The use of optical sensors in a staring mode and optical sensors in a pulsed mode is also presented. The effects of noise are further reduced by employing digital signal processing algorithms to find the heart pulse intermixed with noise signals and present the heart pulse rate in beats per minute on a display. The resulting device permits the visual monitoring of the heart pulse rate in a human body in a consistent, error-free manner.

27 Claims, 4 Drawing Sheets

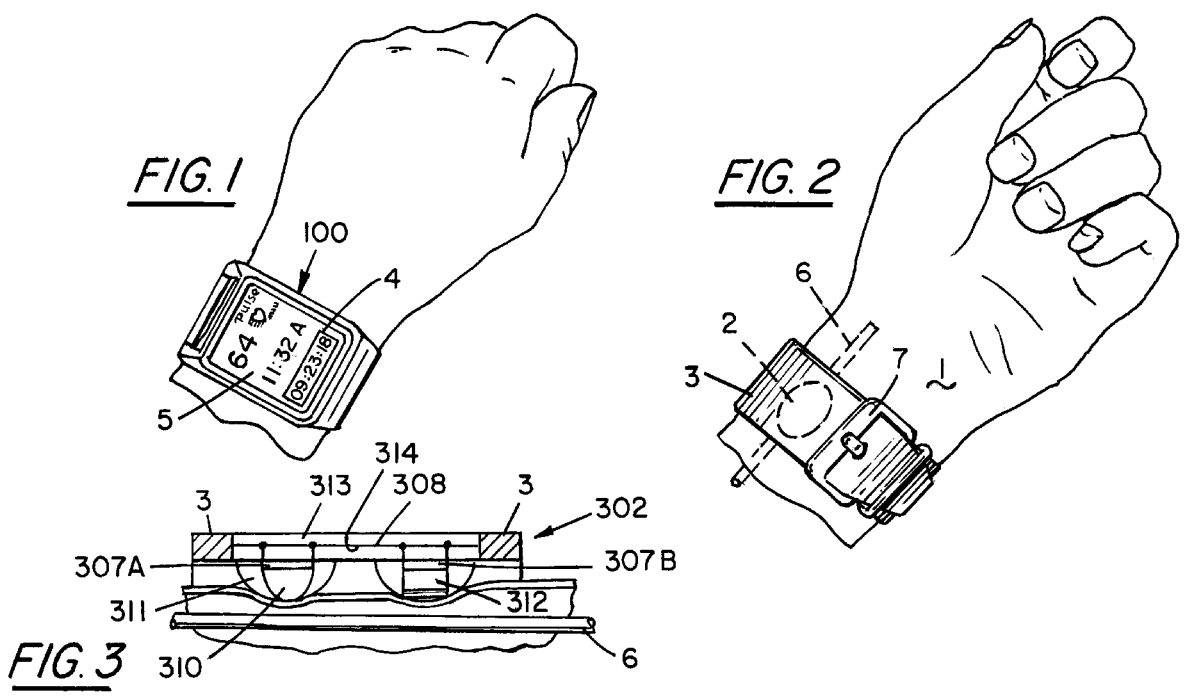
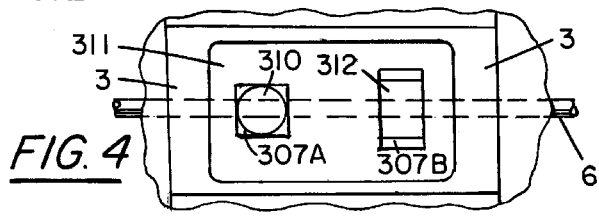
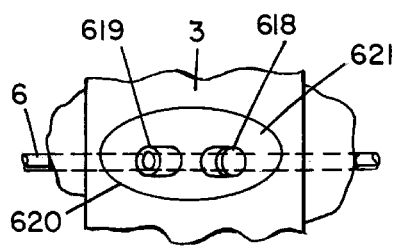
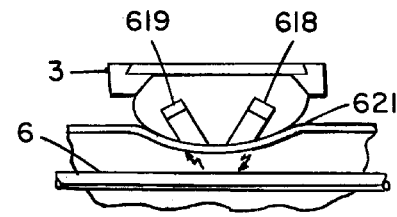
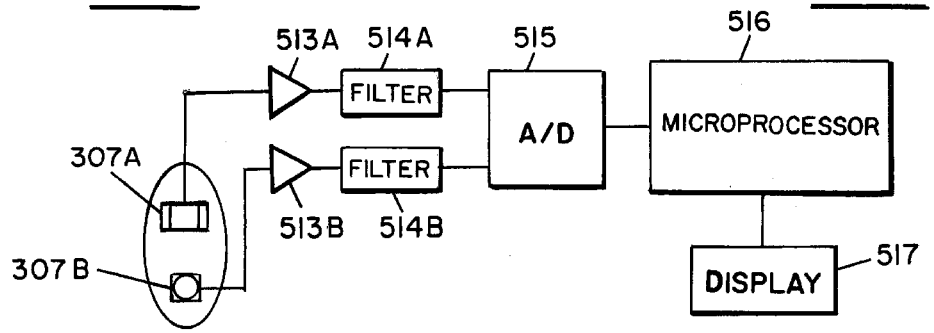

HEART PULSE MONITOR

This is a Continuation-In-Part of application Ser. No. 08/462,152, pending filed on Jun. 5, 1995, which is a Continuation of application Ser. No. 08/252,605, filed Jun. 1, 1994 now abandoned.

BACKGROUND

1. Field of the Invention

This invention relates to heart pulse monitors, in general, and, more particularly, to a heart pulse monitor that is worn by the user, for example at the wrist, and is capable of accurate measurement and display of the user's heart pulse rate (and variation thereof) during physical exercise or other activity.

2. Prior Art

Today, there is a substantial interest in physical well-being and exercising. In conjunction therewith, electronic equipment is employed in health care institutions and by persons during athletic training for monitoring of a person's heart pulse activity. One important measurement parameter is the rate of occurrence of heart pulsations. In healthy persons, the pulse rate is substantially uniform throughout the duration of an activity. However, the rate may vary with changes in the person's activity when the heart may be called upon to pump at a higher or a lower rate. The rate of pulse change during increasing or decreasing activity is directly related to a person's physical condition. Thus, it will be appreciated that a device providing an accurate measurement of pulse rate is most useful during athletic training as well as for the detection and treatment of disease. Similarly, heart rate monitoring can be used to guide cardiovascular intensity to achieve maximum fitness results within an aerobic exercise regimen.

One device useful for the measurement of heart pulse rate is an electronic unit worn on the wrist. In the past, this has necessitated the use of complex electronic equipment. That is, the accurate measurement of an active person's pulse rate at the wrist is a complex process due to the artifacts produced by body motion. These artifacts are concurrent with the heart pulse and are detected by the heart pulse sensor as noise. In many cases, this noise can produce signals of sufficient amplitude to completely mask the heart pulse signal which is to be measured. In order to mitigate the effects of these body artifacts, it is necessary to filter out and electrically cancel as much of the noise signals occurring in the heart pulse frequency band as possible while retaining the desired pulse signal. This problem must be dealt with effectively over a considerable signal-to-noise ratio range.

In some extreme cases the signal-to-noise ratio (SNR) will become negative even with very effective cancellation techniques. When it is no longer possible to reliably detect the heart pulse rate, it is essential that no attempt is made to display a heart rate reading because of the high probability of introducing inaccuracies. It is better to store and display the last good reading until the severe noise condition is concluded and an accurate reading can be made.

During monitoring sequences it is important that the user be able to receive accurate updates of heart pulse rate frequently. It has been demonstrated that this should occur no more frequently than every five seconds with an update every ten seconds seeming to be optimal. This is important to the user since even in situations where violent physical activity is creating body artifact noise in excess of what can be tolerated by the sensing system, a relatively short period of reduced movement is sufficient to provide an updated, accurate read-out of pulse rate.

Several devices have been proposed for providing a wrist-watch type of heart pulse monitor. U.S. Pat. No. 4,120,269 (Prinz) describes one type of such device, viz. a digital plethysmography which customarily utilizes an infrared light transducer.

U.S. Pat. No. 4,059,118 (Stupay) describes a device which uses an actuator pin pressing against a piezoelectric crystal.

The known devices tend to have several shortcomings. Those devices using optical transducers, such as the digital plethysmographies, consume substantial power in the light emitting elements. Thus, use with a battery is not effective. Devices using piezoelectric transducers typically devote little attention to the substantial noise problems that attend the use of such transducers in this application.

When such a pulse rate monitor is mounted on the wearer's wrist, the pulse signal is, to a significant extent, masked by the concurrent noise signals generated due to body motions. The mechanical transducer responds both to pressure from the wearer's pulse beat and to motion from walking, arm swinging and the like, and does not distinguish between them. However, this response is noise insofar as pulse measurement is concerned. As the Stupay patent teaches, "the patient must remain quiet to avoid noise input" during the period in which the pulse rate is being measured.

Also, if the piezoelectric transducer is not mounted directly over the artery of the user, the pulse signal measured by the device will be significantly reduced in amplitude. Thus, the signal is even more likely to be masked by noise. Typically, noise signals may be as high as 1.0 volt, while the pulse signal may be approximately 0.1 volt. Consequently, prior art wrist watch pulse rate monitors employing piezoelectric transducers have been inaccurate because of this unfavorable signal-to-noise ratio.

U.S. Pat. No. 4,224,948 (Cramer) teaches that when a piezoelectric sensor is used, "the watch must be worn on the volar surface of the wrist but lateral to the tendon chord bundles", so as to obtain a pulse reading from the radial artery in the subpollex depression. Moreover, Cramer requires that "the sensors must be forced into the flesh of the wrist for a reading which situation may be uncomfortable."

U.S. Pat. No. 4,409,983 (Albert) uses a complex arrangement of piezoelectric sensors to develop what is described as relatively noise free signals presented to the input of a microprocessor. This apparatus employs a piezo sensor array which is operated by providing a bending force to one end of the sensor elements. This bending interaction is accomplished by using small pins pushing against the ends of the sensors with coil springs being used to dampen the high frequency noise products. Algebraic analog signal summing is used to create relatively noise free signals at the input the microprocessor in the form of an electrical pulse string having the same rate as the heart pulse. While this embodiment may reduce the attendant body noise, there are other problems caused by the complexity of the sensor systems which tend to make this arrangement impractical for mass production.

Inventions using optical sensors to detect the heart rate pulse at the radial artery on the wrist tend to have many of the same body motion related problems as the piezo sensor systems. Added to the motion induced noise problems is the introduction of noise artifacts that are caused by ambient light conditions. These noise sources can be any electrical or natural light sources, including the sun. However, optical sensors do not tend to detect body transmitted acoustical noise. An effective method of dealing with these noise sources is necessary in order to make accurate heart pulse rate readings while the body is in motion or exposed to changing lighting conditions.

BRIEF DESCRIPTION OF THE DRAWINGS

FIG. 1 show one embodiment of the pulse monitor placed on the user's wrist.

FIG. 2 shows the pulse monitor of FIG. 1 and indicates the placement of the sensor assembly over the artery.

FIG. 3 shows placement of a piezo sensor over the radial artery at the wrist.

FIG. 4 shows the configuration of the sensor assembly and its placement relative to the radial artery.

FIG. 5 is a simplified schematic of the heart rate monitor using piezo sensors.

FIG. 6 shows the construction of the optical sensor assembly and placement thereof over the radial artery.

FIG. 7 shows additional detail of the optical sensor relative to the radial artery.

SUMMARY OF THE INSTANT INVENTION

Figure 8:
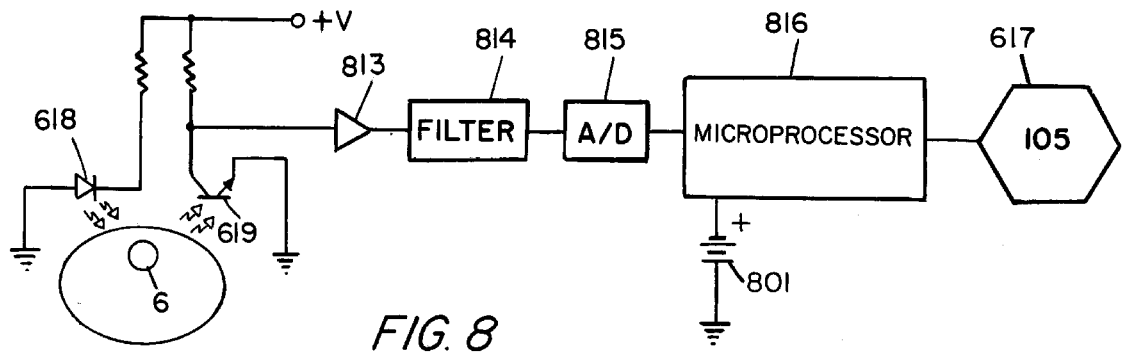
FIG. 8 shows a simplified schematic diagram of one embodiment of the optical pulse rate monitor system.

A pulse rate monitor for sensing a pulse wave produced at an arterial pulse source of the wearer. Piezo pressure sensors or optical sensors outside the surface of the skin produce an electrical signal upon detecting the presence of a pulse in the artery. When using the piezo sensors, a second (background) sensor is employed. Signals from this background sensor are digitally subtracted from the primary pulse sensor thus significantly reducing the effects of body motion signals. Optical sensor configurations typically use only a single sensor. Signals from the sensors are amplified and passed through appropriate filters to reduce the bandwidth of the input circuitry to pass only the signals of interest. The filtered signals are converted to digital signals in a microprocessor. These signals are then digitally processed to produce an output on the display in pulses per minute. The unit may be worn in the same manner as a wrist watch and powered from a small battery. Some embodiments of this device may have all the time keeping capability of a digital wrist watch.

DESCRIPTION OF PREFERRED EMBODIMENT

Referring now to FIG. 1, there is shown a plan view of the simplest contemplated embodiment of the apparatus 100 of the present invention. In this embodiment, the apparatus is configured like a wrist watch. In fact, the apparatus 100 can be combined in a single unit with a wrist watch.

FIG. 2 is taken from a vantage point looking toward the inside of wrist 1 of a user of the device. A sensor assembly 2 containing either optical or piezo sensors is positioned adjacent to the radial artery 6. The assembly 2 is connected to a wrist band 3 adapted to surround and engage the wrist 1. The band 3 is also fastened to a digital wrist watch 4 (see FIG. 1). As described hereinafter, the watch product 4 contains a microprocessor and a display 5. The wrist watch product 4 is disposed on top of the wrist in FIG. 1. The display 5, for example a liquid crystal display (LCD), is shown in side view only.

Referring now to FIG. 2, there is shown the underside of the wrist 1 with the sensor assembly 2 positioned over the radial artery 6 (shown in dashed outline). A clasp mechanism 7 of suitable configuration is used to secure the band 3.

In this embodiment of the invention, it is desirable to have the sensor assembly 2 directly over the radial artery 6 of the wrist (or as close thereto as possible), in order to maximize the signal-to-noise ratio. The sensor assembly 2 is, preferably, positioned over the radial artery 6 in the subpollex depression parallel to the tendon cord bundles on the volar surface of the wrist in order to obtain a reliable pulse reading. If the device is used to monitor pulses in a different artery, e.g. one in the human or animal user's leg, the sensor assembly 2 should be as close as possible to a position directly over that artery.

FIG. 3 shows a side view of a piezo electric sensor assembly 302 placed over the radial artery 6 in the subpollex depression. FIG. 4 shows a plan view of the sensor assembly 302 from the underside. Concurrent reference is made to FIGS. 3 and 4. In this embodiment, the piezo sensors 307A and 307B consist of small ceramic blocks (chips) approximately one eighth inch square, which have been processed to have piezo electrical properties. The sensors 307A and 307B will produce an electrical signal only when pressure is being applied thereto or released therefrom.

The piezo sensor 307A is connected to the electronic control and detection package 313. Attached to the inner surface of the piezo sensor 307A, i.e. the surface facing toward the wrist, is a small button 310. Button 310 is formed of hard plastic and extends to the outer surface of the sensor assembly 302. The button 310 and the chip 307A are encapsulated in a cover layer 311 which is composed of soft silicone or a similar rubber compound that can flex easily, is comfortable to the wearer and provides protection to the sensors from moisture, body fluids, residue and dirt. Button 310 with piezo sensor 307A is adapted to be placed adjacent to the radial artery 6 to detect the heart rate pulse directly therefrom. The soft material of cover layer 311 does not inhibit the action of button 310 pressing against the piezo sensor 307. Typically, this arrangement is sufficient to detect the pulse in the artery 6. However, background noise can be a problem.

However, in a preferred embodiment, a pair of piezo sensors 307A and 307B are utilized to provide the background masking technique. In this preferred embodiment, piezo sensors 307A and 307B are bonded to a common backing plate 308 which can be formed of hard plastic, for example. The backing plate 308 is connected or attached to band 3. In addition, wires 314 connected to each of the sensors pass through the backing plate 308 and are available to be connected to the wrist electronic package 313. Thus, sensor 307A is provided as described supra. In addition, sensor 307B is attached to a bridge assembly 312, typically, fabricated of hard plastic. The bridge 312 is placed along the same axis as the radial artery. However, bridge 312 straddles the radial artery 6 in such a manner that sensor 307B does not detect the pulse in the artery. Rather, only noise from local body motion will be detected by sensor 307B. The soft cover layer 311 is placed over the entire assemblage.

As described supra, the amplified and filtered outputs of piezo sensors 307A and 307B are subtracted electronically in the electronic package 313. This operation minimizes the effects of random body noise in masking the heart pulse signal generated by the pulsing action of the radial artery 6. The effect of the above described sensor configuration is that there is a significant reduction in the noise content of the processed signal.

Referring now to FIG. 5, there is shown a schematic diagram of the major components of the heart rate monitor using piezo sensors. The piezo sensors 307A and 307B are disposed over different portions of the radial artery as depicted in FIG. 4. Electrical signals resulting from mechanical pressure being applied to the surfaces of the piezo transducers 307A and 307B are amplified in pre-amplifiers 513A and 513B. The amplified signals are then passed through switched capacitor low-pass filters 514A and 514B which are, preferably, set to pass frequencies between 0.5 to 4 Hz. The filter assemblies also amplify the signals to a level of approximately one volt for a typical heart pulse signal from the piezo sensors.

The outputs of the filters 514A and 514B are supplied to an analog-to-digital (A/D) converter 515 where the combined signals are converted into a digital word. Typically, 12 bit words are the minimum acceptable; however, 16-bit words are preferred to assure accurate pulse rate readings. The digital words are supplied to the microprocessor 516 where they are temporarily stored. The microprocessor 516 also operates to digitally subtract the background signal produced by sensor 307A from the primary signal produced by sensor 307B. The resultant signal leaves only the difference signal which will normally display a stronger heart pulse reading than the signal found in the background noise reading. The display 517 is connected to the microprocessor 516 and provides the readout of the heart rate along with signal amplitude and time of day information.

Referring now to FIG. 6, there is shown another embodiment of the invention. In this embodiment, the sensor apparatus utilizes optical devices to measure the heart pulse rate from the radial artery 6. The shape of the optical sensor assembly 620 is similar to that of the piezo sensor assembly 302 shown in FIG. 3. In assembly 620, the sensor system consists of an infrared light emitting diode (LED) 618 and a suitable photo detector 619, such as a photo transistor or the like. The LED 618 and the transistor 619 are encapsulated in a lens 621 made of a material which is relatively hard and preferably opaque to ambient light, for example, a dense, black plastic material. An infrared (IR) source, i.e. LED 618, is preferred because IR is easily reflected from the surface of the artery 6. In addition, IR light is outside of the spectral peak of sunlight whereupon the chances of error are reduced, particularly when using the monitor outdoors. The spectral response of the photo transistor 619 must match that of the LED light source 618, of course This can be accomplished by employing optical filters which pass only the desired IR light and absorb visible light from other sources if necessary.

The optical sensor assembly 620 is mounted to the band 3 in order to be positioned along the axis of the radial artery 6 as shown in FIG. 6.

Referring now to FIG. 7, there is shown the relative positioning of the source 618 and sensor 619. The most efficient operation is obtained by directing the light from the LED source 618 and the look angle of the optical sensor 619 at the same point on the artery 6. Sensor output data from the optical transistor 618 is amplified and processed in much the same manner as with the piezo sensors. However, in the optical sensor system there is no separate background sensor shown.

Referring now to FIG. 8, there is shown one embodiment of an optical sensor system. The LED 618 is connected to produce a constant light output which is focused on the radial artery 6. Pulsations of the radial artery (caused by the pumping action of the heart) cause the walls of the radial artery 6 to expand and contract at the heart rhythm rate. These pulsations cause variations (modulation) in the amount of light being reflected from the surface of the artery 6 to the photo sensitive surface of the photo transistor 619. The photo transistor 619 converts the changes in the received light level to a varying electrical signal which is supplied to and amplified by the photo pre-amplifier 813. The output of the photo preamplifier 813 is fed into the filter 814. Typically, filter 814 is a band pass, switched capacitor filter which is band limited to a frequency range of from 0.5 to 4 Hz. The filtered signal is then supplied to the A/D converter 815 and transformed into a digital word. The larger the number of bits in the digital word, the greater the resolution of the pulse capture. In the preferred embodiment, a minimum number of bits is 12, with 15 to 16 bits being highly desirable. The digital word is processed into numerical results by the microprocessor 816. The numerical results are displayed on the LCD 617 as heart beats per minute. A battery 801, typically a wrist watch-type battery (or a lithium battery), is used to provide the power source.

Figure 9:
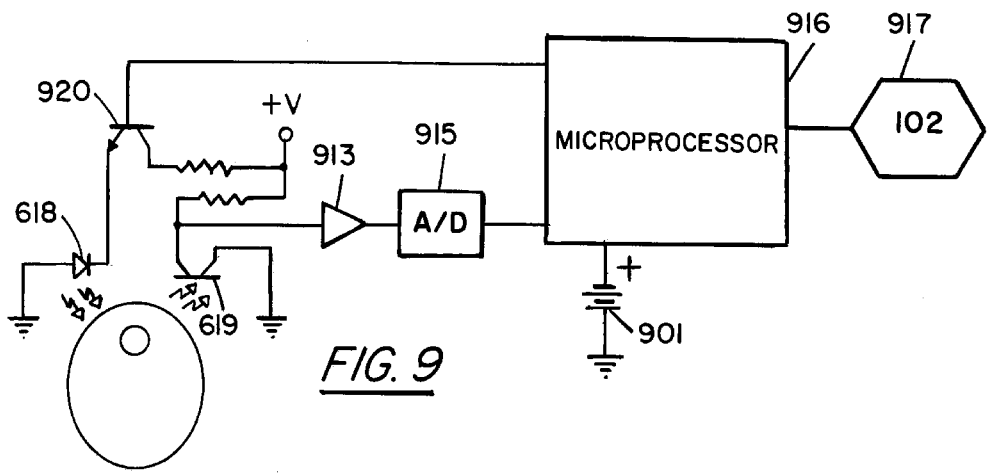
FIG. 9 shows a simplified schematic diagram of another embodiment of the optical pulse rate monitor system.

Referring now to FIG. 9, there is shown another embodiment of the optical sensor design. In this embodiment, the LED 618 and the phototransistor 619 are arranged relative to each other and to the radial artery 6 as described supra. In addition, the conduction path of switching transistor 920 is connected in series with LED 618. The transistor 920 is connected to microprocessor 916 which controls the on/off timing of transistor switch 920. Transistor 920 selectively turns on LED 618. During the interval when LED 618 is turned on and providing illumination to the radial artery 6, photo transistor 619 detects the reflected light signal. This detected signal is amplified in pre-amplifier 913 and supplied to the A/D converter 915 where the signal is converted into a digital word and sent into microprocessor 916. In this embodiment, a low-pass filter is not required inasmuch as the sampling technique provides the filtering necessary to eliminate body motion noise from the signal.

While LED 618 is in the off condition, the ambient light present at the photo sensitive surface of photo transistor 619 is detected. This signal is amplified by preamplifier 913 and digitized by the A/D converter 915. This digital signal is supplied to microprocessor 916 where the "ambient" signal is algebraically subtracted from the "detected" signal generated by the reflected light level from the radial artery 6. Thus, the effect of ambient light noise is removed from the output.

Another feature of this embodiment of the invention is that much less power is required to operate the LED 618. This effectively reduces the power duty factor for the LED by a factor of a hundred or more, thus having the effect of considerably extending the life of battery 901 in the wrist worn instrument. In addition, performance of the unit is improved by maintaining a low discharge rate.

Figure 10:
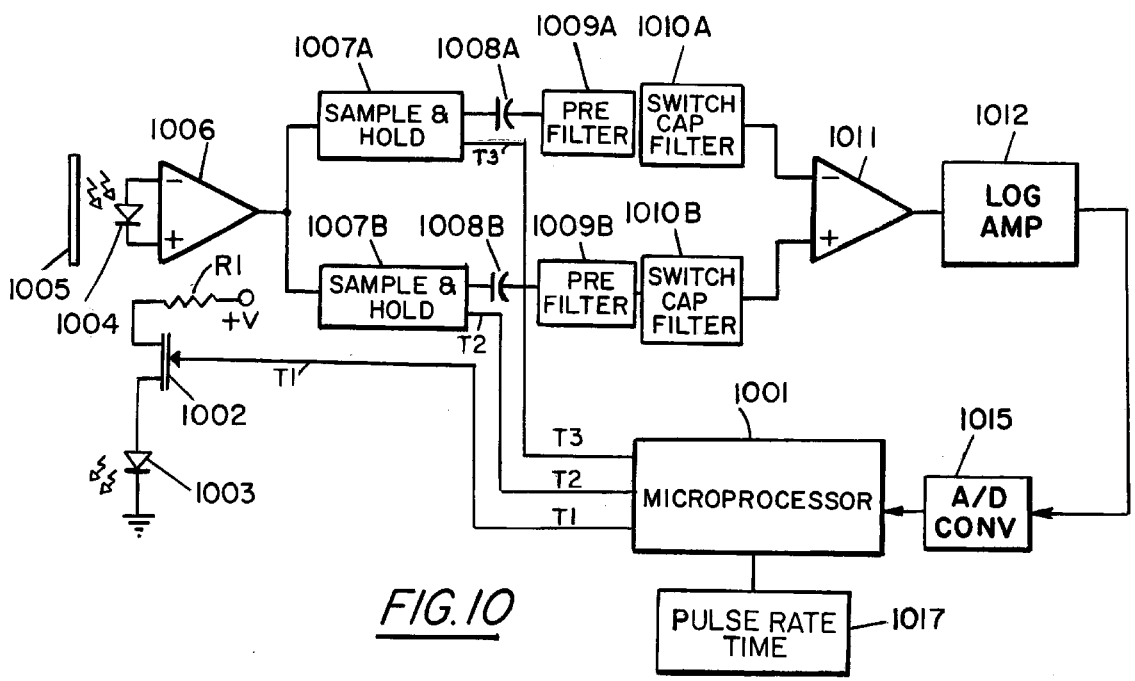
FIG. 10 show another embodiment of the invention using optical sensors.

Referring now to FIG. 10, there is shown another embodiment of the instant invention using optical sensor technology along with signal sampling and background noise cancellation techniques. The principal differences between this embodiment of the invention and the embodiment shown and described relative to FIG. 9 are in the method of capturing and processing the signals obtained from the wrist prior to being converted into digital values.

Microprocessor 1001 generates the timing pulses T1 which selectively turn on MOSFET 1002 which passes a current from +V through $R_1$. This current activates light emitting diode (LED) 1003 for a predetermined period. In one example, a pulse duration of approximately 2 milliseconds with a pulse repetition rate between 100 and 200 Hz was used. Shorter "ON" time duration would have the effect of reducing the average power required to operate the electronics and would be used in battery powered applications. Light emitting diode 1003 is selected for a spectral output which optimizes the signal-to-noise ratio of the pulse being detected by photodetector 1004. The photo detector 1004 can be either a photo-transistor or a photodiode. Either device will function adequately in this application, although a photo-transistor may be more stable and produce noise-free signals. Optical filter 1005 is located adjacent to photodetector 1004. The filter 1005 possesses optical band pass characteristics compatible with the spectral output of the LED 1003. The filter 1005 is used to limit the input light spectrum supplied to photodetector 1004 by transmitting only light from the LED (and any ambient light present within the band pass spectrum). This reduces, and in many cases eliminates, the effects of ambient light present at the wrist during heart rate monitoring. All light wave frequencies outside the band pass limits of the optical filter 1005 are rejected. Similarly, the design of the photo preamplifier 1006 determines whether a photo diode or photo transistor is to be used. In some applications where the full gain capability of the photo transistor can be realized, it is possible to eliminate the photo pre-amplifier 1006 and pass the output signal from the detector directly into the sample and hold circuits 1007A and 1007B.

Sample and hold circuits 1007A and 1007B are used to capture and hold a sample of the output signal from the photo detector 1004 and photo preamplifier 1006. This provides a signal averaging function. Timing pulse T2 is approximately 0.3 milliseconds in duration and occurs approximately 1.7 milliseconds after timing pulse T1 turns the LED 1003 "ON". The 1.7 millisecond sampling delay time duration is required for the comparatively slow responding photo preamplifier 1006 to rise to full amplitude and produce a stable light "N" signal.

Timing pulse T3 is set to occur approximately 0.5 milliseconds second prior to timing pulse T2 and produces a light "OFF" background signal used to determine the intensity of any ambient light present in the detected signal. The background signal is output from sample and hold circuit 1007A. The modulated or changing light level signal from the sample and hold circuits 1007A and 1007B are supplied to pre-filter circuitry 1009A and 1009B via coupling capacitors 1008A and 1008B, respectively. The direct current voltage components of the output signals from sample and hold circuits 1007A and 1007B are removed by capacitors 1008A and 1008B. The capacitors also remove any off-set voltage levels present at the output of the sample and hold circuits. The prefilters 1009A and 1009B are used to remove switching transients and to smooth out step signals from the output of the sample and hold circuits. In one embodiment, the pre-filters were configured as second order, multiple feedback band-pass circuits and provided a signal voltage gain of 15. The prefilters used an undedicated operational amplifier housed in the switched capacitor filters integrated circuit packages 1010A and 1010B. The 3 dB cutoff frequency of the prefilters was set at 24 Hz. The filters also act as an anti-aliasing filter for the switched capacitor filters, thus removing any unwanted harmonic signals. Typically, the switched capacitor filters 1010A and 1010B are 8th order band-pass filters with the band pass set at 0.5 to 5 Hz. This band pass corresponds to a heart rate input range from 30 to 240 beats per minute.

The output of switched capacitor filter 1010A contains the background or ambient light modulation information and is supplied to the inverting input of differential amplifier 1011. The output of switched capacitor filter 1010B contains the heart rate modulated signal and the ambient light modulated signal and is supplied to the non-inverting input of the differential amplifier 1011. The resultant output signal from differential amplifier 1011 is the heart pulse signal minus the ambient light signal. This design provides approximately 60 dB of common mode rejection or approximately a 1000:1 rejection ratio. This rejection ratio has proved adequate for the test unit to be operated with the optical components exposed to light from incandescent and fluorescent lighting as well as sunlight. In cases where the circuitry was operated with the LED turned "OFF" all the time, virtually no interference from ambient lighting was observed at the output of differential amplifier 1011 while being operated in a normally illuminated room.

Log amplifier 1012 is employed to extend the dynamic range of the analog pulse processing system. Signals from the sensors at the wrist will vary in amplitude from a few millivolts to a volt or more at the output of differential amplifier 1011. These signals which have nearly 60 dB of dynamic range, would be difficult to capture and process if presented directly to analog to digital converter (A/D) 1015. The log amplifier 1012 employed herein employs logarithmic amplifier principles, and is designed to perform as a Log-n (rather that Log-10 or Log-e amplifier). This amplifier provides a relatively high gain to low level signals and compresses the output of higher amplitude signals. Thus, those signals introduced into the system as noise caused by body motion or ambient light artifacts do not exceed the input range of A/D converter 1015. The dynamic range of the log amplifier 1012 employed in the above described embodiment of this invention is approximately 40 dB. Other gain ratios may be required to properly implement variations of this same functional configuration.

Microprocessor 1001 accepts and stores the digital output of the A/D converter 1015 and processes the data using the same algorithms as for the piezo and steady state light embodiments of the invention described supra. Pulse rate in beats per minute along with time is displayed on LCD 1017 which is connected to the microprocessor 1001.

Figure 11:
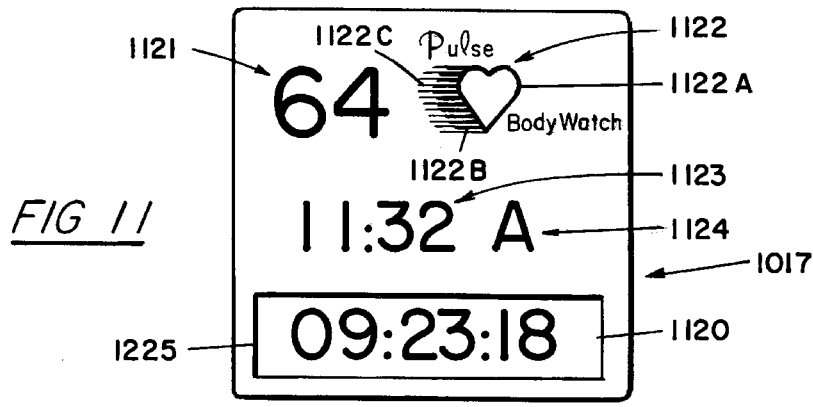
FIG. 11 shows one embodiment of the layout and functions contained in the liquid crystal display.

FIG. 11 shows one proposed layout of the liquid crystal display 1017 (see FIGS. 9 and 10, for example). This layout is representative only and is not intended to be limitative. For example, the pulse rate is displayed at digits 1121 in the upper left corner of the display. The heart-shaped logo 1122 is also a functional element of the display. The heart logo 1122 is composed of three segments 1122A, 1122B and 1122C which indicate relative signal level from the sensor placed over the artery. The graduated lines 1122B and 1122C at the left side of the heart logo 1122 are, in essence, a bar graph which indicates the level of the detected pulse signal from the sensor. This graphic display will provide the wearer with an analog indication of when the sensor is properly and optimally placed over the artery to assure accurate and continual heart pulse rate readings. That is, the closer the position of the sensor to the optimum, the more the bar graphs are illuminated.

Numerals 1123 on the LCD 1017 indicate the time of day and letter 1124 selectively indicates "A" (for AM) or "P" (for PM).

The numerals 1225 inside of the box 1120 indicate time, interval time in seconds, the date (in a dd:mm:yy format) or any other information desired. The inclusion of the time keeping and calculator functions with the pulse monitor are illustrative only. These functions can be omitted if desired. Likewise, other functions can be incorporated into the display if so desired.

Figure 12:
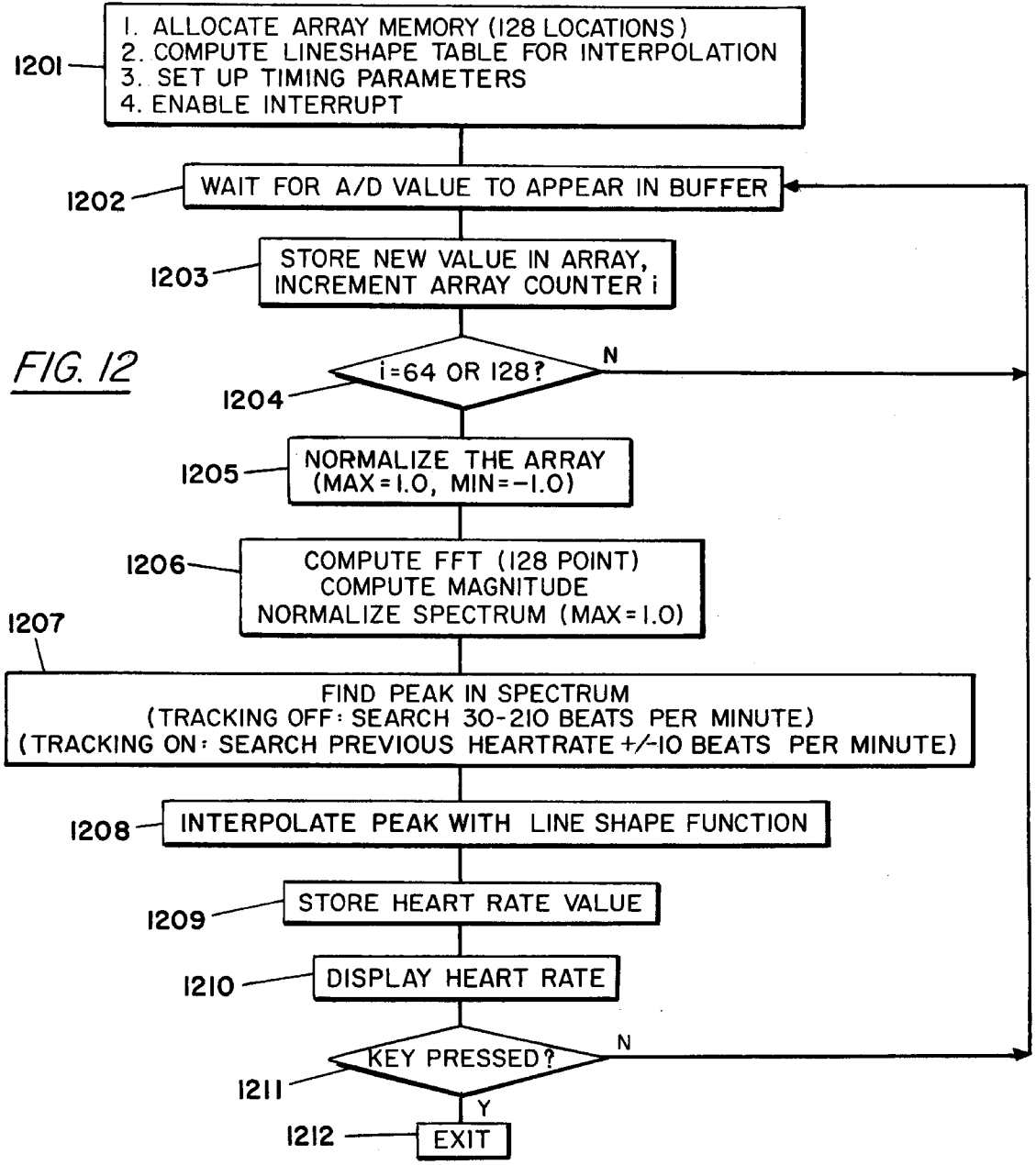
FIG. 12 shows a flow diagram of the basic software/processor functions on the heart rate monitor.

FIG. 12 provides a flow chart of the software functions contained in the preferred embodiment of the invention. The functions are represented by a plurality of boxes. The piezo and the optical configurations both use the same data processing and display software. This software, with its attendant data processing functions, causes the pulse meter to function properly in a relatively high level noise environment caused by body motion. The software is designed to look for frequency node peaks within a computed spectrum. It determines the highest peak within a specified region of the spectrum which, in most cases, is the heart pulse and tracks this peak value. In cases where totally divergent values are computed, the reading on the display will not be updated until a value within the range of the initially acquired and computed data is again realized. Without these software functions this unit would be just another pulse monitor that would not track the heart pulse at the radial artery unless the body was being held nearly motionless.

Upon initialization of the processor, the functions indicated in block 1201 are initiated. Step one is to allocate memory for the digitized (e.g. 16 bit) word heart pulse data from the A/D converter 1015 (see FIG. 10). Math functions in the program used to compute the curve fitting table used in the program are set up in Step two. In Step three the timing parameters for the system are set up. These timing parameters determine the samples per second and the number of total samples to be taken in a single data acquisition sequence. Typically, taking 128 12-bit data samples in 10 seconds is satisfactory. That is, approximately 10 seconds are required to gather enough data to be able to make an accurate reading. The interrupt channel is enabled in Step four. The interrupt selectively activates the A/D converter 1015 to take a sample of data. Once these initialization steps are completed, the system is ready to begin acquiring and processing heart pulse data from A/D converter 1015.

In response to an interrupt signal, the A/D converter 1015 takes a 12-bit sample from the amplified sensor output signal. This sample represents the difference in response of the photosensor with the LED "on" and the LED "off". The electronic amplifier creates the required difference signal automatically for the processing software. The digital data representative of the difference signal are loaded into the memory buffer represented by box 1202.

In the situation where the software is being operated in an optional personal computer (PC), for example in a test mode, the new value can be displayed on the PC terminal screen. However, watch format applications (as described herein) will, typically, employ a dedicated special function microprocessor using optimized machine software code to implement data processing and display functions. In this mode, the new value represented by the digital data produced by an interrupt signal is stored in a memory array as represented by box 1203. In Array 1 the data is sorted into the (i)th location.

As noted supra, a 10 second sample is used to gather data. However, different techniques can be used to increase the rate at which the display is updated from 10 seconds to 5 seconds. For example, with one memory array having 128 sample bins the heart display array can be updated only once per 10 second sampling period with a fully new data set, as it has been established that 10 seconds of heart rate data are required to reliably track the heart pulse while the body is in motion. However, by monitoring the array index counter, the display can be updated after collecting data for T seconds (T=10), by using T seconds of newly acquired data, and 10-T seconds of "old" data in the processing.

The method for displaying the heart rate every 5 seconds is as follows. A single memory array is allocated with 128 memory locations. When a sample is acquired, it is placed into an array location pointed to by the array index counter: N. The software monitors the value of N. When N=128, the contents of the memory array are sent to the FFT processing algorithm, with the "oldest" sample at location #1, When N=64 (assuming more than one data collection cycle has occurred), the data in the array is sent to the processing algorithm in a reordered format, where the data at location N=64 . . . 128 are moved to locations 1 . . . 63, and the data at location N=1 . . . 63 are moved to locations 64 . . . 128. Note that this reordering process must occur outside of the collection array, for example, by placing the reordered data into a secondary array so that the original contents and order of the collection array are not altered. The reordered data is then sent to the processing algorithm. Thus, the heart rate displayed at a 5 second interval represents a 10 second collection period, but 64 of the samples are "new" and 64 of the samples were included in the previous heart rate computation.

Clearly, this method can be used to implement other rates of display by sending the data to the processor at shorter intervals than the 64 sample period. The method is not limited to the 5 second update rate described above. For example, if data were processed when i=32, 64, 96 and 128 samples, a 2.5 second update rate could be achieved.

Box 1204 represents the process test to see if the array counter is either 64 or 128 (as described above). If the condition is not satisfied (as indicated by N), the system will loop back and acquire another differenced data point from A/D converter 1015 and continue doing so until the array is filled.

Figure 13:
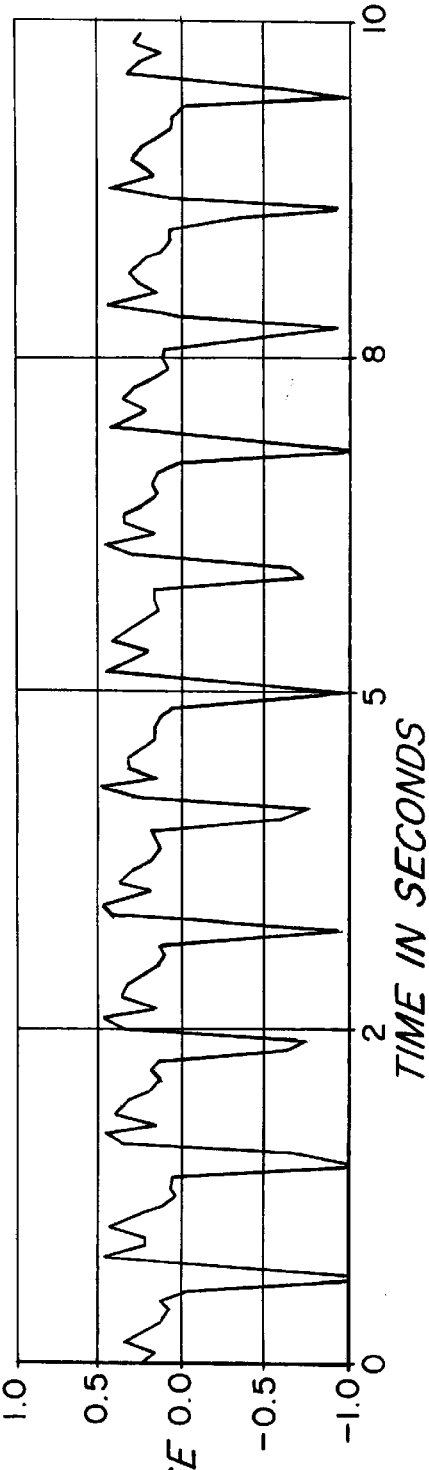
FIG. 13 a graphical respresentation of a normalized sample vs time chart.

Once the array is filled (i.e. N=64 or 128), the data is normalized to a maximum value of 1.0 and a minimum value of −1.0 as shown in box 1205. This is done to assure that there are no highly divergent values in the data array that could cause overflow errors in the routine. For example, these signals can range from 1 to 256 before normalization. (A typical normalized signal is shown in the Sample vs Time signal representation in FIG. 13.)

The specific mathematical method used to detect the pulse signal is the Fourier Transform (FT). This method, as represented by box 1206, decomposes the input signal into a spectrum of frequencies of which the input signal was composed. The strength of the spectrum at a specific frequency is proportional to the level of that frequency in the input signal. The FT is an ideal filter for the heart pulse signal because the heart pulse is a regular periodic event, whereas sources of noise signals (such as ambient light) or artifacts (such as the creaking of joints), for example, tend to occur in a non-periodic way. However, the FT is able to distinguish a small periodic pulse in the midst of relatively large sources of noise. That is, the pulse signal is concentrated in a narrow spectral range, and the noise is spread over the entire spectral range.

The heart watch data generation is specifically designed to operate with a FT analysis basis. The bandwidth of the input signal is cut off at frequencies above 5 Hz, as described supra, which removes the possibility of "aliasing" in which higher frequency signals are sampled at rates too low to resolve them, thereby creating irreconcilable artifacts in the frequency spectrum. The sample rate of 12.8 samples/sec, and the 10 second sample integration period are designed to provide a 128 sample array. The FT operates most efficiently on data sets which are $2^N$ in size. In the embodiment contemplated herein, N=8. The 10 second integration period (a) provides a spectral resolution of 6 beats per minute between adjacent spectral points, and (b) is short enough to be a reasonable estimate of the user's present heart rate. The data sampling rates, bandpass pre-filtering, and FT algorithm are optimized to provide a useful measurement of the heart rate, yet are conservative of the limited processing resources typical of a microprocessor environment.

The computational algorithm for the FT is the Fast Fourier Transform (FTT). The specific FTT algorithm can be a reduction in time algorithm, a reduction in frequency algorithm or any other algorithm which implements the Fourier Transform (FT). The spectral data is returned from the FTT as complex numbers which are converted to a real magnitude by computing the complex absolute value. The data is normalized as shown in box 1206 by finding the peak value in the initial tracking range between 30 and 210 beats per minute. All spectral values in this range are divided by the peak value so that the peak value equals 1.00 and all other values are less than 1.00. This peak value represents the strongest periodic value in the spectrum, and is assumed to be the heart pulse signal.

A pulse tracking feature is designed in the pulse monitor to minimize the chance of displaying a spurious peak value in the data stream. This tracking feature is referred to in box 1207. In the "tracking off" mode, the user initializes the tracking system and obtains a steady pulse reading in the range of 30 to 210 beats per minute which enables accurate pulse tracking. The tracking system then narrows the tracking range from the initial limits of 30 and 210 beats per minute, to ±10 beats per minute centered on the latest valid pulse measurement. Thus, only heart rate values that are within a range of 20 beats per minute of the last reading are possible. The center of this tracking range is set to the latest heart rate, so that the pulse monitor is able to track the user's heart rate over wide ranges as it rises and falls during exercise or other activity.

The heart rate taken from the peak value determined in step 1207 is, thus, accurate to 6 beats per minute. The accuracy of the pulse rate is improved by an interpolation process represented by box 1208 which compares the shape of the actual spectral peak to a theoretical approximation. The theoretical pulse signature should conform to a line shape of the form:

$$S(x) = \frac{\sin^2 \pi * x}{(\pi * x)^2}$$

where x is the distance from the theoretical peak center.

Figure 14:
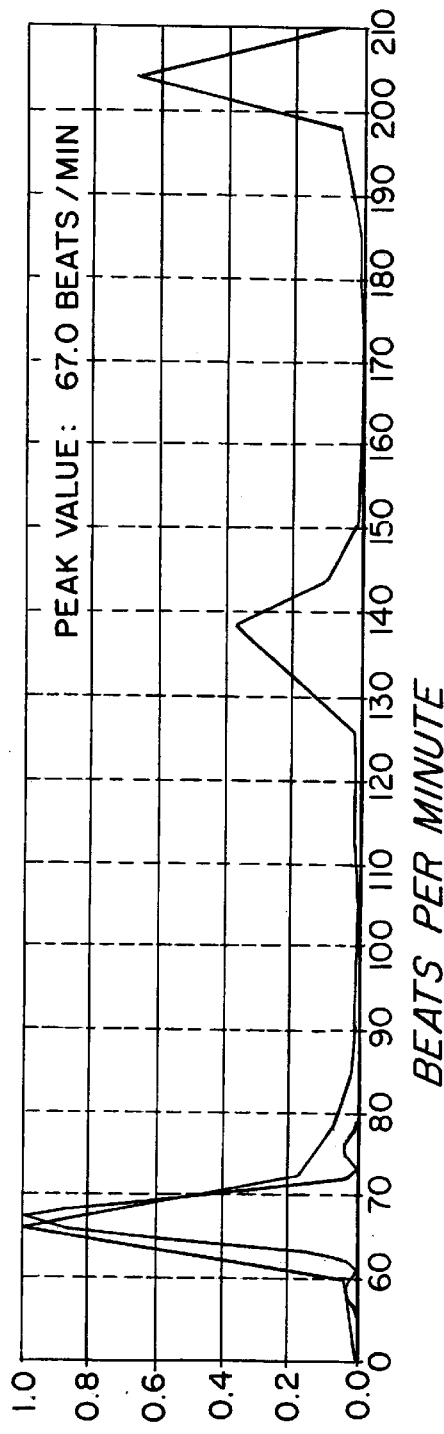
FIG. 14 is a graphical representation of a frequency distribution of signal.

In this point of the process, the approximated peak line-shape is computed at 1 beat per minute intervals, and stepped across the actual peak at a one beat per minute step interval. A typical representation of the interpolation process is shown in FIG. 14. At each step the sum of absolute differences between the overlapping points of the actual and theoretical peak is tabulated. When this difference is a minimum, i.e. where the actual and theoretical peaks have the best fit or match, the center of the theoretical peak is at the interpolated heart rate, which is accurate to within 1 beat per minute.

A suggested in box 1209, the system determines the peak value in the spectrum which is from 0.5 to 4 Hz. The system, e.g. a microprocessor, converts the peak value into a signal indicative of pulses per minute. This information is stored in a suitable storage mechanism in the system. This heart rate is displayed on the LCD display 1017 (as indicated in block 1210) in the pulse location 1021 on the heart watch. Alternatively, the information can be displayed on a PC terminal screen (not shown).

At the decision step represented by box 1211, the software determines if the program has been terminated, for example by pressing the initialization or start key. If not, (as indicated by N) the entire sequence will be repeated again.

If the process is terminated, as detected in decision step of box 1211, the microprocessor exits the routine as indicated at box 1212 and the heart watch is turned off.

As described above, FIG. 13 is a graphical representation of samples vs time which has been normalized to maintain the signal range within reasonable limits. The chart shown is a plot of voltage versus time and shows a fairly uniform configuration.

As described above, FIG. 14 shows a graphical representation of a frequency distribution of signals. The chart shown is a plot of normalized magnitude vs beats per minute. The highest peak is centered around a value of about 60–70 beats per minute. The other peaks of any size are clearly the harmonics of the basic beats per minute value. These harmonics can be ignored or discarded by the system.

Thus, there is shown and described a unique design and concept of a heart pulse monitor. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

We claim:

1. A heart pulse rate monitor assembly adapted to be worn by a user, typically at the wrist, to measure the user's heart pulse rate, comprising;

sensor means for sensing heart pulses of the user and producing a varying electrical sensor signal representative of said heart pulses;

amplifier means connected to said sensor means for amplifying said electrical sensor signal;

signal modification means connected to said amplifier means for converting said sensor signal into a digital signal;

array means for storing values of said digital signal, first normalizing means for normalizing said values of said digital signals to eliminate any highly divergent values stored in said array means, FFT means for computing the FFT of said values of said digital signals to detect the strength of a specific frequency in a spectrum of frequencies included in said varying electrical sensor signal, second normalizing means for normalizing the FFT within a selected range of heart pulses, pulse tracking means for selecting a steady pulse reading within said selected range of heart pulses and within a limited range of pulse rates as computed from the FFT which pulse is representative of the user's heart pulse, display means connected to said pulse tracking means for selectively displaying the presence and the rate of the heart pulse;

housing means for enclosing said sensor means, said amplifier means, said signal modification means and said display means in a single unit; and mounting means for attaching said housing to the user.

2. The monitor recited in claim 1 wherein, said means for sensing comprises an optical sensor device.

3. The monitor recited in claim 2 wherein, said optical sensor device includes a light emitting means for shining light onto the pulse location of the user and a light detecting means for detecting light reflected from said pulse location of the user.

4. The monitor recited in claim 3 wherein, said light emitting means comprises a light emitting diode and said light detecting means comprises a photodetector, said light emitting diode and said photodector are spaced apart adjacent to said pulse location.

5. The monitor recited in claim 4 wherein, said light emitting diode produces infrared light and said photodetector is responsive to the same type of light.

6. The monitor recited in claim 1 wherein, said display means comprises a liquid crystal display.

7. The monitor recited in claim 1 wherein, said housing comprises in a wrist watch case.

8. The monitor recited in claim 1 wherein, said sensor means includes means for sensing ambient noise signals separately from said sensor signal, and subtractor means for subtracting said ambient noise signal from said sensor signal to produce a heart pulse signal.

9. The monitor recited in claim 8 wherein, said subtractor means operates on digital representations of said ambient noise signal and said sensor signal.

10. The monitor recited in claim 1 wherein, said filter means comprises low pass filters.

11. A pulse rate monitor comprising, sensor means adapted to be disposed adjacent to a pulse location of a user, said sensor means operative to produce a first signal in response to a pulse at said pulse location and a second signal in response to artifact signals at said pulse location, circuit means connected to said sensor means to receive said first and second signals, said circuit means operative to produce a digital output signal which is representative of the difference between said first and second signals and is a function of the rate at which said first signal is received, said circuit means compares said difference signal to a theoretical approximation signal to produce an output signal which is the best match between said difference signal and said theoretical approximation signal;

display means connected to said circuit means and operative to produce a display signal which is representative of said output signal, and housing means for enclosing said sensor means, said amplifier means, said signal modification means, said circuit means and said display means in a single unit.

12. The monitor recited in claim 11 wherein, said sensor means comprises a piezo electric sensor means.

13. The monitor recited in claim 5 wherein, said piezo electric sensor means includes first and second piezo electric sensor devices, said first piezo electric sensor device mounted with a button to contact said pulse location, said second piezo electric sensor device mounted on a bridge which is spaced from said pulse location.

14. The monitor recited in claim 13 wherein, each of said first and second piezo electric sensor devices is connected to said circuit means.

15. The monitor recited in claim 13 wherein, both of said first and second piezo electric sensor devices are mounted on a common backing plate.

16. The monitor recited in claim 11 wherein, said circuit means includes microprocessor means for processing the first and second signals.

17. The monitor recited in claim 16 including, analog-to-digital converter means connected to supply input signals to said microprocessor means.

18. The monitor recited in claim 17 including, filter means connected to supply input signals to said analog-to-digital converter means.

19. The monitor recited in claim 18 including, amplifier means connected to supply input signals to said filter means.

20. The monitor recited in claim 19 including, sample and hold circuit means for capturing and holding the input signals supplied by the amplifier means connected between said amplifier means and said filter means.

21. The monitor recited in claim 20 including, timing control means connected between said circuit means and said sensor means for controlling the operation of the circuit means.

22. The monitor recited in claim 18 including, log amplifier means connected between said filter means and said analog-to-digital converter to provide selective signal compression.

23. The monitor recited in claim 11 including, switching means connected between said circuit means and said sensor means whereby said circuit means selectively turns off said switching means such that said first signal is not supplied to said circuit means whereby said second signal is algebraically subtracted from said first signal in said circuit means.

24. The monitor recited in claim 23 including, sample and hold circuit means connected between said sensor means and said filter means in order to capture and hold a sample of said sensor signal produced by said sensor means.

25. The monitor recited in claim 24 including, differential amplifier means connected to said sample and hold circuit means to produce an output signal which is the difference between said first signal and said second signal.

26. A pulse rate monitor comprising:

sensor means adapted to be disposed adjacent to a pulse location of a user, said sensor mean operative to produce a first signal in response to the occurrence of a heart pulse at said pulse location and a second signal in response to artifact signals at said pulse location; and circuit means operative to produce an output signal which is representative of the difference between the first and second signals which varies as a function of the heart pulse rate;

wherein said circuit means includes:

amplifier means connected for amplifying the signals from the sensor means and supplying the amplified signals as output signals;

filter means connected to receive the output signal of the amplifier means and provide a filtered signal as a filter output signal;

an analog-to-digital converter connected to receive the filter output signal and convert said filter output signal to a digital signal;

microprocessor means connected to receive said digital signal from said analog-to-digital converter;

said microprocessor means includes:

array means for storing values of said digital signal;

first normalizing means for normalizing said values of said digital signals between selected maximum and minimum value;

means for computing the Fourier Transform (FT) of said values of said digital signals in order to detect a periodic pulse representative of a frequency node peak having a narrow spectral range relative to the entire spectral range;

pulse tracking means for selecting a pulse from the FT within a predetermined signal spectrum, which pulse is representative of the user's heart pulse rate, and supplying the pulse rate as an output;

a display means connected to said microprocessor means for displaying the pulse rate;

wherein said microprocessor means only updates the display means when said pulse tracking means selects a peak in said predetermined spectrum; and wherein said microprocessor means does not update said pulse rate a divergent value of said peak is selected.

27. The method of detecting a heart pulse rate with a unitary portable detector comprising, detecting a heart pulse signal from a pulse location on the user's body, converting the heart pulse signal to a digital signal, storing the digital signal in a buffer, periodically updating the digital signal stored in the buffer, normalizing the digital signal stored in the buffer to establish a limited range of values for the digital signal, computing a Fourier Transform to filter the normalized signal to detect a periodic pulse in the normalized signal and to eliminate a periodic pulses in the normalized signal;

converting the frequency of said periodic pulse to a spectral peak value which is representative of said heart pulse signal, comparing said spectral peak value to a prescribed line shape function and interpolating to achieve the best match therebetween in order to obtain an accurate representation of the heart pulse rate; and displaying the heart pulse rate on a suitable display.

\* \* \* \* \*